United States Patent [19]
Solomon

[11] 3,948,602
[45] Apr. 6, 1976

[54] ANALYTICAL METHOD OF MONITORING AIR FOR CHLOROMETHYL ETHER

[75] Inventor: Richard A. Solomon, Midland, Mich.

[73] Assignee: The Dow Chemical Company, Midland, Mich.

[22] Filed: Sept. 4, 1973

[21] Appl. No.: 393,765

Related U.S. Application Data

[63] Continuation-in-part of Ser. No. 327,184, Jan. 26, 1973, abandoned.

[52] U.S. Cl. .......... 23/232 C; 23/230 M; 23/230 L; 23/232 E; 23/255 E; 55/67; 55/386
[51] Int. Cl.$^2$........................................ G01N 31/08
[58] Field of Search.......... 23/232 C, 232 E, 230 L, 23/254 EF, 255 E; 55/67, 386

[56] References Cited
UNITED STATES PATENTS

| | | | |
|---|---|---|---|
| 3,230,046 | 1/1966 | Beroza.............................. | 23/232 C |
| 3,374,660 | 3/1968 | McKinney et al.................. | 23/232 C |
| 3,740,195 | 6/1973 | Lietzau.............................. | 23/230 R |
| 3,807,217 | 4/1974 | Wilkins et al..................... | 23/232 C |
| 3,837,806 | 9/1974 | Ritter et al....................... | 23/230 R |

OTHER PUBLICATIONS

Gaylord, Norman G.; Polyethers Part I Polyalkylene Oxides and Other Polyethers; Interscience Publishers dio. of John Wiley & Sons; New York, N.Y., 1963; pp. 433 and 434.

*Primary Examiner*—Barry S. Richman
*Assistant Examiner*—Dale Lovercheck
*Attorney, Agent, or Firm*—Earl D. Ayers; Edward E. Schilling; Glenn H. Korfhage

[57] ABSTRACT

Apparatus and method for monitoring air to determine the presence of chloromethyl methyl ether at the part per billion level.

The above compound is reacted with an alkali metal salt of an alcohol, a phenol, or a chlorophenol to form a derivative which provides suitable sensitivity when applied to a gas chromatograph utilizing a suitable detector such as a hydrogen flame detector or, if a chlorophenol reactant is used, an electron capture detector.

6 Claims, 1 Drawing Figure

U.S. Patent   April 6, 1976   3,948,602
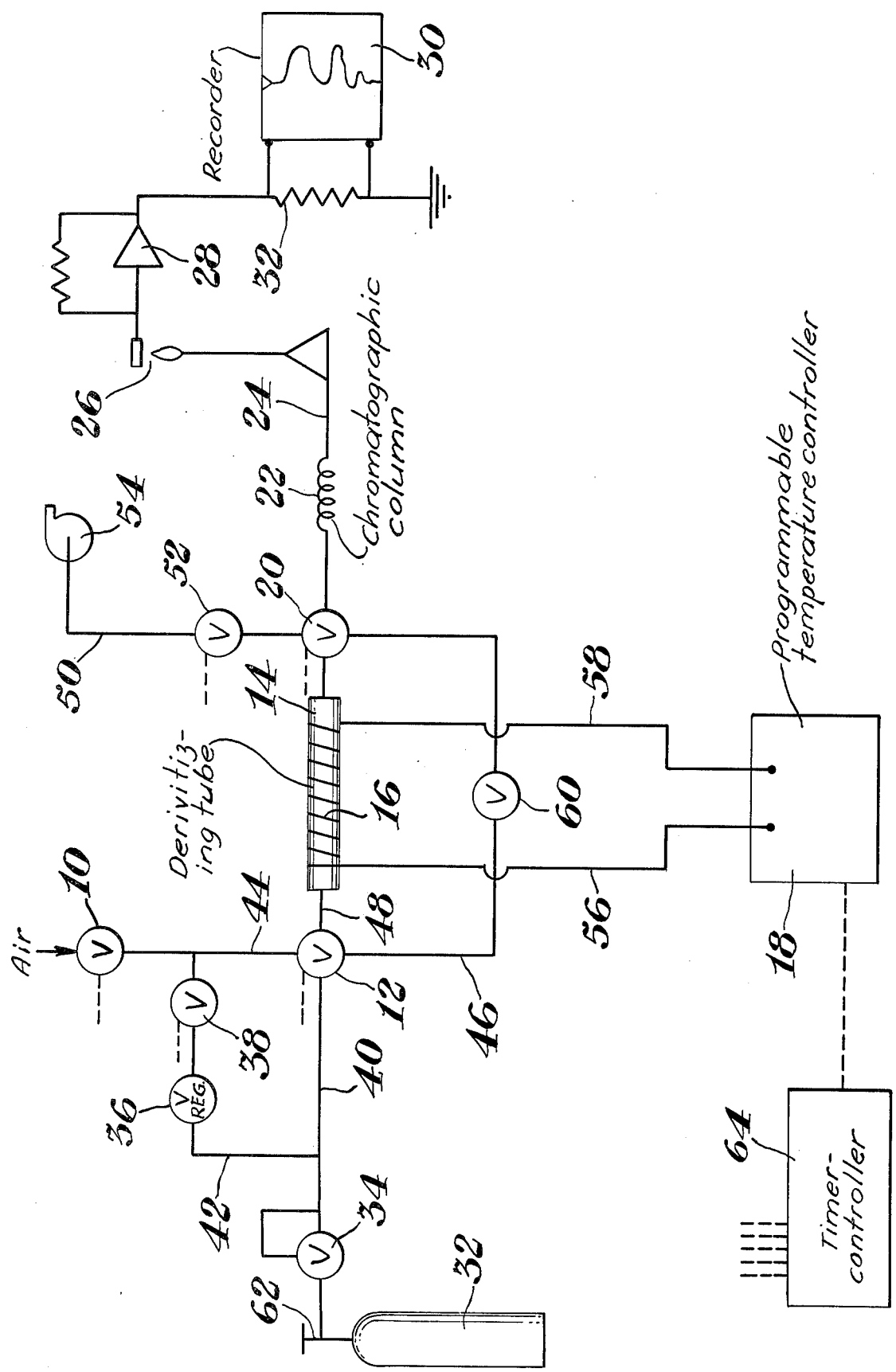

ANALYTICAL METHOD OF MONITORING AIR FOR CHLOROMETHYL ETHER

This is a continuation-in-part of co-pending application Ser. No. 327,184, filed Jan. 26, 1973, for Analytical Apparatus and Method, now abandoned.

BACKGROUND OF THE INVENTION

This invention relates to an air monitoring method, and particularly to a method for determining the presence of chloromethyl methyl ether in air at the part per billion level, or less.

Experience indicates that the direct analysis of chloromethyl methyl ether is not adequate in sensitivity or specificity for monitoring this compound in environmental air in the parts per billion concentration range.

OBJECTS OF THE INVENTION

Accordingly, a principal object of this invention is to provide an improved method for monitoring the presence of chloromethyl methyl ether in air at the per billion level.

STATEMENT OF INVENTION

In accordance with this invention, chloromethyl methyl ether is reacted with an alkali metal salt of an alcohol, a phenol, or a chlorophenol. The derivative is then passed through a gas chromatograph having a suitable detector. The detector output signal is then coupled, usually through an amplifier, to a recorder or other readout device.

BRIEF DESCRIPTION OF THE DRAWING

The invention, as well as additional objects and advantages thereof, will best be understood when the following detailed description is read in connection with the accompanying drawing which, in diagrammatical form illustrates an apparatus for carrying out this invention.

DETAILED DESCRIPTION OF THE DRAWING

Referring to the drawing, there is shown apparatus including a valved air inlet 10 coupled via line 44 to a four way valve 12. A tank 32 of carrier gas such as nitrogen, for example, has a valve 62 which is coupled through pressure regulator valve 34 and line 40 to an input of the four way valve 12. A line 42 carrying pressure regulating valve 36 and valve 38 is coupled to the line 44 and to the line 40 between the valve 34 and the valve 12.

One output of the valve 12 is coupled via line 48 to a derivatizing tube 14 which is between one and four inches in length and is packed with beads on which is deposited an alkali metal salt of an alcohol or a phenol, or for formation of a derivative detectable by an electron capture detector, a chlorophenol. The tube 14 may be heated by any suitable means, such as, for example, the heater winding 16 which is coupled through leads 56 and 58 to, and is energized from a suitable programmable temperature controller 18.

The output of the derivatizing tube 14 is coupled to an input of the four way valve 20.

An output of the valve 12 is coupled through the line 46 which couples valve 60 to another input of the valve 20.

One output of the valve 20 is coupled through line 50, carrying valve 52, to a vacuum pump 54.

The other output of the valve 20 is coupled through the line 24 to a flame detector 26 through a chromatographic column 22.

The output of the flame detector 26 is coupled to amplifier 28 and the output signal developed across the load resistor 32 is coupled to a recorder 30 or other readout device.

OPERATION

In operation, air to be sampled passes through valves 10 and 12, through the derivatizing tube 14 and then through valves 20 and 52 to the vacuum pump 54.

Simultaneously, pressure regulated inert carrier gas, usually nitrogen, passes from the tank 32 through line 40, valve 12, line 46, valve 20 through the chromatographic column 22, through line 24, and through the flame detector 26.

After a suitable amount of air is drawn through the derivatizing tube 14, air flow is stopped by closing valve 10. At this time, valve 38 is opened, allowing carrier gas from the tank 32 to flow through line 42, needle valve 36, line 44, valve 12, derivatizing tube 14, valve 20, line 50 and the vacuum pump 54. This results in the purging of residual air from the derivatizing tube 14.

After suitable purging time with the flow of carrier gas through the tube 14, valves 38 and 52 are shut off. Heat is then applied to the derivatizing tube 14 through the electrical heater winding 16, for example. After a suitable temperature is attained in the tube 14 (as sensed by the temperature controller 18) to volatilize derivative compounds in the tube 14, valves 12 and 20 are operated to allow carrier gas from the tank 32 to flow through the pressure regulator 34 and line 40 through the tube 14 and on through the chromatographic column 22, carrying the volatilized derivatives with it. Chromatographic separation of the volatilized derivative is accomplished in the column 22 and the separated derivative is combusted in a suitable detector 26 such as a hydrogen flame detector. The output signal from the detector 26 is amplified by amplifier 28 and displayed on the readout device, recorder 30.

After all the volatilized derivative has been swept through the chromatographic column 22, the heater winding 16 is de-energized and the derivatizing tube 14 allowed to cool at near ambient temperature. Valves 12 and 20 are actuated to again permit the flow of air through the tube 14 to the vacuum pump 54 on opening of the valves 10 and 52.

The actuation of valves 10, 12, 20, 38 and 52, all of which are electrically controllable, are controlled by a suitable timer-controller 64 which is coordinated with the temperature controller 18.

The following reaction may be used to stabilize chloromethyl methyl ether and also to enhance its sensitivity.

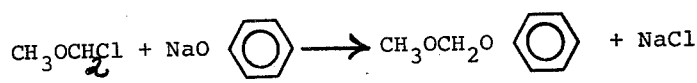

In this reaction the sodium phenate is carried on glass beads or other suitable non-reactive particulate material. Sodium salts of chlorinated phenols may also be used in place of the sodium phenate in the above reactions.

Other derivatives which may be formed and detected in analyses in accordance with this invention are:

$CH_3OCH_2Cl + NaOCH_2CH_3 \longrightarrow CH_3OCH_2OCH_2CH_3 + NaCl$

In this reaction the sodium ethoxide is carried on glass beads or other suitable non-reactive particulate material.

Other sodium alkoxides could be used in place of the sodium ethoxide, as may sodium chlorophenates.

Stated broadly, alkali metal salts of an alcohol, or a phenol such as a chlorophenol may be reacted with chloromethyl methyl ether to produce a stable derivative which has enhanced sensitivity as compared to CMME when passed through a hydrogen flame detector.

The alkali metal salts of an alcohol are prepared as a methanolic solution and are then evaporated onto the supporting material, 60/80 mesh glass beads, for example. The beads are then placed in the derivatizing tube 14, a short glass tubular member (between 1 and 4 inches in length is common). One derivatizing column 14 used is 3 inches long and has an internal diameter of about 3/16 inch.

The derivatizing column 14 should be close coupled to the valve 20, preferably by a glass tube. The other lines used in the apparatus may be made of stainless steel, copper, polytetrafluoroethylene or other material which is non-reactive with the components passing through it.

Hydrogen flame detectors made by Varian, Beckman Instrument Co., and Hewlett-Packard have been found to be suitable. A 1 millivolt recorder 30 is commonly used. However, other suitable readout devices may be substituted.

The chromatograph 22 may be a Varian Aerograph Model 1400 gas-liquid chromatograph for batch-wise analytical work. A Beckman Model 320 DF process gas liquid chromatograph or Bendix Corp. Model 6000 process gas chromatograph or other similar chromatographs are well suited for automated analytical work in accordance with this invention.

While a hydrogen flame detector would be usable for the detection of all the derivatives, the electron capture detector would be operable with those derivative compounds containing chlorine.

If a chlorophenol is used in the derivatizing tube, a much smaller sample volume may be used. For example, a milliliter of CMME containing sample may be passed through a heated (around 140° C.) derivatizing tube and run directly through the chromatograph column.

What is claimed is:

1. A method for determining the presence of chloromethyl methyl ether in air at the part per billion level, comprising reacting chloromethyl methyl ether from the air with an alkali metal salt of an alcohol or a phenol, wherein said salt is contained on a solid support for reaction with said chloromethyl methyl ether, to form a dechlorinated methyl methyl ether substitution reaction product, passing the reaction product through a gas chromatographic column, then eluting the reaction product therefrom through a detector therefor and displaying the output of said detector on a readout device.

2. A method in accordance with claim 1, wherein said alkali metal salt is sodium phenate.

3. A method in accordance with claim 1, wherein said alkali metal salt is sodium ethoxide.

4. A method in accordance with claim 1, wherein said alkali metal salt is a sodium salt of a chlorinated phenol.

5. A method in accordance with claim 1, wherein said alkali metal salt is a sodium alkoxide.

6. A method in accordance with claim 1, wherein said alkali metal salt is a salt of a chlorophenol.

* * * * *

UNITED STATES PATENT AND TRADEMARK OFFICE
CERTIFICATE OF CORRECTION

PATENT NO. : 3,948,602
DATED : April 6, 1976
INVENTOR(S) : Richard A. Solomon

It is certified that error appears in the above-identified patent and that said Letters Patent are hereby corrected as shown below:

In the title, on the cover page and at the top of Column 1, change "Analytical Method of Monitoring Air for Chloromethyl Ether" to --Analytical Method of Monitoring Air for Chloromethyl Methyl Ether--.

On the cover sheet, under "Other Publications", line 3, delete "dio." and insert --div.--.

Signed and Sealed this

Thirteenth Day of July 1976

[SEAL]

Attest:

RUTH C. MASON
Attesting Officer

C. MARSHALL DANN
Commissioner of Patents and Trademarks